(12) United States Patent
Hanieh et al.

(10) Patent No.: US 11,001,608 B2
(45) Date of Patent: May 11, 2021

(54) ARID5A PEPTIDE INHIBITORS

(71) Applicant: KING FAISAL UNIVERSITY, Hofouf (SA)

(72) Inventors: Hamza Naim Ahmad Hanieh, Aqaba (JO); Abdullah Mossa Alzahrani, Hofouf (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 16/508,601

(22) Filed: Jul. 11, 2019

(65) Prior Publication Data
US 2021/0009636 A1    Jan. 14, 2021

(51) Int. Cl.
*C07K 7/06* (2006.01)
*C07K 5/00* (2006.01)
*A61K 38/07* (2006.01)
*A61K 38/08* (2019.01)
*A61P 29/00* (2006.01)
*C07K 5/10* (2006.01)
*A61K 38/00* (2006.01)

(52) U.S. Cl.
CPC .............. *C07K 7/06* (2013.01); *A61K 38/07* (2013.01); *A61K 38/08* (2013.01); *A61P 29/00* (2018.01); *C07K 5/10* (2013.01); *A61K 38/00* (2013.01)

(58) Field of Classification Search
CPC ...................................... C07K 7/06; C07K 7/08
See application file for complete search history.

(56) References Cited

U.S. PATENT DOCUMENTS

| 5,858,675 | A | 1/1999 | Hillman et al. |
| 9,109,023 | B2 | 8/2015 | Wang |
| 9,957,295 | B2 | 5/2018 | Wang |
| 2018/0016576 | A1 | 1/2018 | Kishimoto et al. |
| 2018/0195064 | A1 | 7/2018 | Kishimoto et al. |

FOREIGN PATENT DOCUMENTS

WO    WO2016183509 A1 * 11/2016
WO    WO 2018/013907 A1 *  1/2018 ............... C07K 7/06

OTHER PUBLICATIONS

Estell et al., Geneseq: BDJ32548 (2016).*
Zaman et al., "Arid5a exacerbates IFN-γ-mediated septic shock by stabilizing T-bet mRNA," PNAS, 113(41) pp. 11543-11548 (2016).
GenBank: AYM55650.1: cytochrome p450 [Croton stellatopilosus](Oct. 24, 2018).
Hanieh, Hamza et al., "Arid5a stabilizes OX40 mRNA in murine CD4+ T cells by recognizing a stem-loop structure in its 3'UTR", European Journal of Immunology, 48: pp. 593-604 (2018).
Masuda, Kazuya et al., "Arid5a regulates naive CD4+ T cell fate through selective stabilization of Stat3 mRNA", Journal of Experimental Medicine, 213(4): pp. 605-619 (2016).
International Search Report and Written Opinion dated Oct. 15, 2020 in PCT/IB2020/056569.

* cited by examiner

*Primary Examiner* — Robert C Hayes
(74) *Attorney, Agent, or Firm* — Nath, Goldberg & Meyer; Richard C. Litman

(57) ABSTRACT

AT-rich interactive domain-containing protein 5a (Arid5a) inhibitors can include mid-sized peptides (peptides having less than 15 amino acids) that inhibit the activity of Arid5a. The peptides include the sequence of SEQ ID NO: 1. In an embodiment, the Arid5a peptide inhibitors can include a peptide having a sequence selected from the group consisting of SEQ ID NO: 2, SEQ ID NO:3, and SEQ ID NO:4. The Arid5a peptide inhibitors can be useful for experimental investigation and treating a disease or disorder, such as, inflammation, diseases associated with inflammation, cancer, and autoimmune disease.

4 Claims, 5 Drawing Sheets

Specification includes a Sequence Listing.

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Synthetic construct

<400> SEQUENCE: 1

Ala Cys Thr Val
1

<210> SEQ ID NO 2
<211> LENGTH: 8
<212> TYPE: PRT
<213> ORGANISM: ARTIFICIAL SEQUENCE
<220> FEATURE:
<223> OTHER INFORMATION: Synthetic Construct

<400> SEQUENCE: 2

Ala Cys Thr Val Gly Gly Tyr Glu
1               5

<210> SEQ ID NO 3
<211> LENGTH: 8
<212> TYPE: PRT
<213> ORGANISM: ARTIFICIAL SEQENCE
<220> FEATURE:
<223> OTHER INFORMATION: Synthetic Construct

<400> SEQUENCE: 3

Glu Glu Ala Cys Thr Val Gly Gly
1               5

<210> SEQ ID NO 4
<211> LENGTH: 11
<212> TYPE: PRT
<213> ORGANISM: ARTIFICIAL SEQUENCE
<220> FEATURE:
<223> OTHER INFORMATION: Synthetic Construct

<400> SEQUENCE: 4

Ala Cys Thr Val Gly Gly Tyr Glu Asp Gly Asp
1               5                   10
```

```
<210> SEQ ID NO 5
<211> LENGTH: 100
<212> TYPE: PRT
<213> ORGANISM: Mus musculus

<400> SEQUENCE: 5

Gln Glu Glu Glu Gln Ala Phe Leu Val Ser Leu Tyr Lys Phe Met Lys
1               5                   10                  15

Glu Arg His Thr Pro Ile Glu Arg Val Pro His Leu Gly Phe Lys Gln
            20                  25                  30

Ile Asn Leu Trp Lys Ile Tyr Lys Ala Val Glu Lys Leu Gly Ala Tyr
        35                  40                  45

Glu Leu Val Thr Gly Arg Arg Leu Trp Lys Asn Val Tyr Asp Glu Leu
    50                  55                  60

Gly Gly Ser Pro Gly Ser Thr Ser Ala Ala Thr Cys Thr Arg Arg His
65                  70                  75                  80

Tyr Glu Arg Leu Val Leu Pro Tyr Val Arg His Leu Lys Gly Glu Asp
                85                  90                  95

Asp Lys Pro Leu
            100

<210> SEQ ID NO 6
<211> LENGTH: 22
<212> TYPE: RNA
<213> ORGANISM: Artificial Sequence
<220> FEATURE:
<223> OTHER INFORMATION: Based on Homo Sapiens

<400> SEQUENCE: 6
uccacaccgu ucuaggugcu gg                                              22

<210> SEQ ID NO 7
<211> LENGTH: 28
<212> TYPE: RNA
<213> ORGANISM: Artificial Sequence
<220> FEATURE:
<223> OTHER INFORMATION: Based on Homo Sapiens

<400> SEQUENCE: 7
ugcaguggcu uguguucugg ccacugca                                        28

<210> SEQ ID NO 8
<211> LENGTH: 8
<212> TYPE: PRT
<213> ORGANISM: Artificial Sequence
<220> FEATURE:
<223> OTHER INFORMATION: Synthetic construct

<400> SEQUENCE: 8

Gly Thr Tyr Gly Cys Glu Val Ala
1               5
```

ARID5A PEPTIDE INHIBITORS

The Applicants hereby incorporate by reference the sequence listing contained in the ASCII text file titled 32087_14_sequence_ST25.txt, created Jan. 17, 2019 and having 3 KB of data.

BACKGROUND

1. Field

The disclosure of the present patent application relates to RNA binding protein inhibitors, and particularly to peptides capable of inhibiting the activity of Arid5a.

2. Description of the Related Art

Inflammation is a complex response of the body to the harmful stimuli that involves primarily immune cells and molecular mediators. Based on duration and components of the immune response, inflammation is classified into acute and chronic. Chronic inflammation is the prolonged form of inflammation, which is mediated primarily by mononuclear phagocytes such as macrophages and lymphocytes including T cells. These cells produce pro-inflammatory cytokines and other pro-inflammatory mediators that cause more lasting responses manifested by tissue damage and fibrosis and inflammatory diseases.

Extracellular stimuli induce signaling pathways inside the immune cells that ends with transcription and translation of pro-inflammatory mediators to exacerbate inflammation. For example, macrophages contribute to chronic inflammation by secretion of pro-inflammatory cytokines such interleukin-6 (IL-6), IL-23, and tumor necrosis factor-α (TNF-α), and T helper-17 (Th17) cells contribute to autoimmunity by secretion of IL-17. A myriad of studies have been directed toward targeting IL-6 or inhibition of its functions as a promising therapeutic strategy, owing to its critical roles in differentiation of IL-17-producing Th17 cells, and pathogenesis of many disorders such as autoimmune diseases and cancer. Tocilizumab, humanized monoclonal antibodies against IL-6 receptor, has been approved to treat autoimmune diseases such as rheumatoid arthritis and decrease Th17 cells frequency. Moreover, targeting IL-6 by Siltuximab, humanized anti-IL-6 antibodies, shows therapeutic potential in Castelman disease and various human cancers. Inhibition of signal transducer and activator of transcription 3 (STAT3), a transcription factor in IL-6 signaling promotes Th17 cell differentiation, reversed the IL-6-mediated impairment of regulatory T (Treg) cell suppression in multiple sclerosis (MS) patients.

The gene expressions of Il6, STAT3, and Il17 are tightly regulated at transcriptional and posttranscriptional levels. Therefore, targeting the molecules that directly and/or indirectly promote their expression has emerged as a fascinating strategy for potential treatment of inflammatory, autoimmune diseases, and cancer.

AT-rich interactive domain-containing protein 5a (Arid5a), an RNA-binding protein, is required for inflammation and autoimmunity. It exacerbates the experimental model of MS by stabilizing the mRNAs of Il6 and OX40 through physical binding to their 3' untranslated region (3'UTR). Arid5a promotes differentiation and effector functions of Th17 cells by stabilizing the STAT3 and OX40 mRNAs through recognizing stem-loop (SL) structures in their 3'UTR. In addition, Arid5a promotes IL-17 signaling by controlling mRNA stability and translation. Although Arid5a has emerged as a therapeutic target in inflammatory and autoimmune diseases, peptide/protein inhibitors of Arid5a have not been previously identified.

Thus, peptide inhibitors targeting Arid5a solving the aforementioned problems is desired.

SUMMARY

AT-rich interactive domain-containing protein 5a (Arid5a) inhibitors, or Arid5a peptide inhibitors, can include mid-sized peptides (peptides having less than 15 amino acids) that inhibit the activity of Arid5a. The peptide inhibitors can inhibit the RNA-binding activities of Arid5a to target SLs and production of pro-inflammatory cytokines. The Arid5a inhibitors can be useful for in vitro and in vivo experimental investigation, and for treating diseases associated with inflammation, autoimmune diseases, and cancer. The peptide inhibitors for Arid5a can include the sequence of ACTV (SEQ ID NO: 1). In an embodiment, the Arid5a peptide inhibitors can include one or more sequences selected from the group consisting of ACTVGGYE (SEQ ID NO: 2; herein, PIA), EEACTVGG (SEQ ID NO:3), and ACTVGGYEDGD (SEQ ID NO:4).

These and other features of the present teachings will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
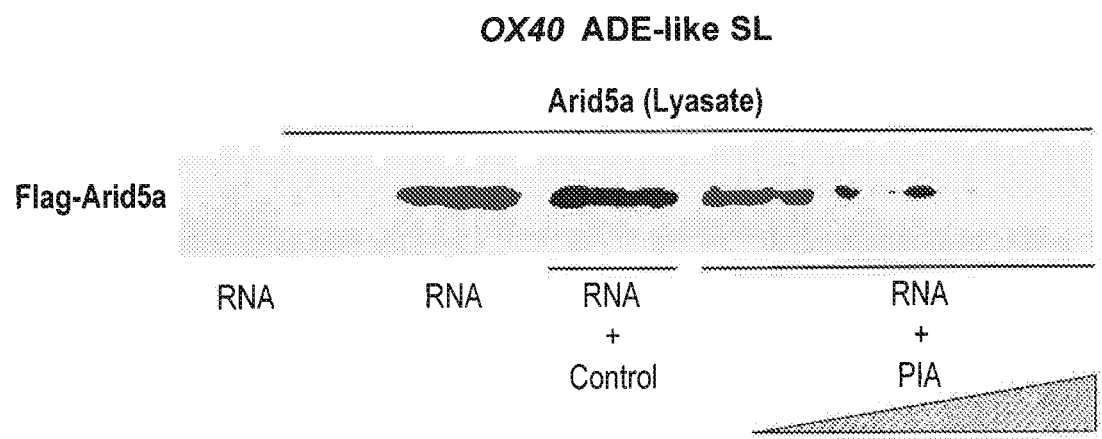
FIG. 1A is an immunoblot image showing the inhibitory effects of PIA on Arid5a (Flag-Arid5a) binding to alternative decay element (ADE)-like SL in OX40 3'UTR in the presence of PIA.

As used herein, a "subject" includes mammals, e.g., humans, dogs, cats, sheep, cows, rats, mice, and the like.

As used herein, "Arid5a" refers to AT-rich interactive domain-containing 5a (Arid5a), a protein that stabilizes mRNAs encoding pro-inflammatory mediators, including signal transducer and activator of transcription 3 (STAT3), 11-6, and OX40 (CD134).

Arid5a inhibitors include peptides that inhibit the activities of Arid5a, an RNA-binding protein. In an embodiment, the peptides can include mid-sized peptides, e.g., peptides having less than 15 amino acids. The Arid5a inhibitors include the amino acid sequence ACTV (SEQ ID NO: 1). For example, the Arid5a inhibitors can include a peptide having one or more sequences selected from the group consisting of ACTVGGYE (SEQ ID NO: 2), EEACTVGG (SEQ ID NO: 3), and ACTVGGYEDGD (SEQ ID NO: 4).

Arid5a has previously been shown to exacerbate inflammation in experimental MS by stabilizing the mRNAs of Il6 and OX40, and subsequently protein production. Arid5a enhances differentiation of Th17 cells and production of IL-17, a hallmark cytokine in MS patients by endowing stability to STAT3 and OX40 mRNAs through association with conserved SLs in their 3'UTRs. In addition, Arid5a counteracts the anti-inflammatory function of Regnase-1 and/or Roquin-1 by competition on the SLs of STAT3 and OX40. Also, Il-6, OX40, and STAT3, the targets of Arid5a, promote tumorigenesis, and thus targeting these molecules directly and/or indirectly exerts anti-tumor effects. Deletion of Arid5a in mice has been shown to robustly ameliorate development of experimental MS and septic shock, and inhibition of Arid5a by chlorpromazine (CPZ) demonstrated therapeutic potential in septic shock and lung inflammation.

The PIA (SEQ ID NO:2) described herein inhibit RNA-binding activities of Arid5a to the conserved stem loops (SLs) in the 3' untranslated region (UTR) of mRNAs encoding pro-inflammatory mediators and inhibit production of pro-inflammatory cytokine. For example, PIA can inhibit the physical association of Arid5a to the ADE-like SL in the 3'UTRs of OX40 mRNAs, and can inhibit physical binding of Arid5a to an identified SL in the 3'UTR of STAT3 mRNAs. PIA can also reduce IL-17 production by differentiated Th17 cells.

In an embodiment, the Arid5a peptide inhibitors can inhibit physical binding of Arid5a to the 3'UTR of mRNAs encoding pro-inflammatory mediators by interacting with a target domain of Arid5a. In particular, the Arid5a peptide inhibitors can inhibit physical binding of Arid5a to the 3'UTR of target mRNAs by targeting Pocket X of Arid5a. Pocket X of Arid5a includes, but is not limited to, Glu53, Phe56, Leu57, Val58, Leu84, Tyr88, Leu133, Val134, Tyr137, Val138, His140, and Leu141 (SEQ ID NO: 5). According to an embodiment, PIA (SEQ ID NO.: 2), interacts with Arid5a through the amino acid residues 56-58, 133-134, and 137 of Pocket X, and reduces production of IL-17 by differentiated Th17 cells. Arid5a peptide inhibitors can target Arid5a via Pocket X and its interacting residues, which in turn, can enhance the RNA-destabilizing functions of Regnase-1 and/or Roquin-1.

The PIA is a highly efficient inhibitor that abrogates physical binding of Arid5a to SLs in the 3'UTR of mRNAs encoding pro-inflammatory mediators. Accordingly, the PIA and other ACTV (SEQ ID NO: 1)-containing peptides can be useful for in vitro and in vivo experimental investigation, and for treating a disease or disorder, such as inflammation, diseases associated with inflammation, autoimmune disease, and cancer.

A pharmaceutical composition can include one or more of the Arid5a peptide inhibitors (SEQ ID NO: 1, SEQ ID NO: 2, SEQ ID NO: 3, and SEQ ID NO: 4) and a pharmaceutically acceptable carrier. Carriers are inert pharmaceutical excipients, including, but not limited to, binders, suspending agents, lubricants, flavorings, sweeteners, preservatives, dyes, and coatings. The pharmaceutically acceptable carrier can include, for example, water, alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

The present compositions can be in their original forms or modified forms. The modifications comprise, but are not limited to, chemical modification, incorporation in cyclic peptide, and addition of cell-penetrating peptides. The present compositions can be used in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for in vitro and in vivo experimental investigation and for administration to a subject for treating a disease or disorder, such as, inflammation, diseases associated with inflammation, autoimmune disease and cancer.

The present teachings are illustrated by the following examples.

Example 1

Experimental Conditions

In Silico

The sequence of mouse Arid5a (NP_001165676.1) was obtained from NCBI (https://www.ncbi.nlm.nih.gov/protein/). The residues 50-149 were used to build the Arid5a 3D model. The Pocket X was used as a target binding site for molecular docking simulation. Pocket X was confirmed using Q-site Finder and Pocket Finder.

In silico docking was carried out using SYBYLX 2.1 software (Tripos Associates Inc.). The CHEMPLP scoring function was applied. The Arid5a peptide inhibitors (SEQ ID NO: 1, SEQ ID NO: 2, SEQ ID NO: 3, SEQ ID NO: 4) and selected residues of Arid5a were set flexible for docking. The flexible Arid5a residues included Leu57, Val58, Leu60, Tyr61, Iso71, Iso82, Leu85 and Leu133.

Arid5a-Expressing Plasmids

The Flag-tagged pcDNA 3.1-plasmid was used to clone mouse Arid5a cDNA (WT; ENSMUST00000115032.7) at Xba1 and Ecor1 restriction sites, as previously described. Sequential substitution mutations were introduced to pcDNA 3.1 plasmid-expressing WT Arid5a using Mutagenesis kit (Thermo), following manufacturer's instructions. The mutations in WT Arid5a included substitution of Phe56 (TTC) with Cys (TGC), Leu57 (CTG) with Ala (CGC), Val58 (GTC) with Ala (GCC), Leu133 (CTG) with Ala (CTG), Val134 (GTC) with Ala (GCC) and Tyr (TAT) with Ala (GCT). All mutant proteins were detected by immunoblotting using anti-Arid5a monoclonal antibodies (Thermo).

RNA-Protein Binding Assay

The synthesized 3'-biotinylated RNA of OX40 ADE-like SL (5'-UCCACACCGUUCUAGGUGCUGG-3') (SEQ ID NO: 6) and STAT3 SL (5'-UGCAGUGGCUUGUGUUCUGGCCACUGCA-3') (SEQ ID NO: 7) (Invitrogen)

were conjugated to streptavidin beads. The PIA (SEQ ID NO: 2) and scramble amino acids (Control, GTYGCEVA (SEQ ID NO: 8)) were purchased from LifeTein Co. The Flag-Arid5a enriched lysate of HEK293T cells was mixed, washed, and proteins bound to the RNA were eluted for immunoblotting. The Arid5a protein was detected by SDS-PAGE using anti-Flag mouse monoclonal antibodies (Sigma-Aldrich). Quantification of bands intensities was carried out using ImageJ v.1.48 software (http://imagej.nih.gov/ij/download.html).

Differentiation of Th17 Cells

Naïve CD4$^+$ T cells were isolated from the spleen using MACS® CD4$^+$CD62L$^+$ isolation kit (Miltenyi Biotec). The isolated CD4$^+$CD62L$^+$ T cells were cultured in the presence of anti-CD3/CD28 dynabeads (Invitrogen), IL-6 (30 ng/mL; R&D Systems), transforming growth factor TGF-β1 (4 ng/mL; R&D Systems), anti-interferon IFN-γ and anti-IL-4 (10 μg/mL; Biolegend) for 72 h.

Statistics

The intensities of Arid5a immunoblot bands and IL-17 concentrations are presented as mean±SD from at least three independent experiments produced similar results. The statistical significance between mean values was tested by one-way ANOVA. *$p<0.05$ was considered significant.

Example 2

In Silico Docking of PIA Against Pocket X of Arid5a

Analysis of Arid5a in silico confirmed that it contains five binding pockets, of which only one pocket (Pocket X) showed the highest drugability score. Therefore, docking of candidate peptide inhibitors against Arid5a was limited to Pocket X.

Molecular docking simulation results revealed potential bindings between Arid5a and PIA (SEQ ID NO: 2). The potential binding included a number of ionic and hydrogen bonds and Pai interactions between PIA and residues in Pocket X with binding score (ChemPLP 83.42). Further, in silico investigation revealed that changes in the amino acids ACTV (SEQ ID NO: 1) in PIA by omission or substitution or sequence order abolish the potential interaction with Arid5a. In line with the significance of the ACTV sequence, two mid-sized peptides, EEACTVGG (SEQ ID NO: 3) and ACTVGGYEDGD (SEQ ID: NO: 4) showed potential interaction with Pocket X of Arid5a with the score of ChemPLP 82.85 and ChemPLP 58.88, respectively, and omission or substitution or changing the order of the ACTV sequence abolishes the interaction. Together, the ACTV (SEQ ID: NO: 1) sequence in Arid5a peptide inhibitors is essential for potential interaction with Pocket X.

Example 3

OX40 ADE-Like SL (RNA)-Protein (Arid5a)-Binding Assay

The 3'-biotinylated RNA of OX40 ADE-like SL (5'-UCCACACCGUUCUAGGUGCUGG-3') (SEQ ID NO: 6) was conjugated to streptavidin beads. The biotinylated RNA-streptavidin conjugate was mixed with lysates of HEKT293 cells transfected with pcDNA3.1 expressing Flag-Arid5a (wild-type; WT) in the presence of scramble peptide (Control SEQ ID NO: 8) or PIA (SEQ ID NO: 2) (20, 40 and 60 μM), washed, and eluted for detection by immunoblotting. Anti-Flag monoclonal antibodies were used to detect Flag-Arid5a in the eluates.

Figure 1B:
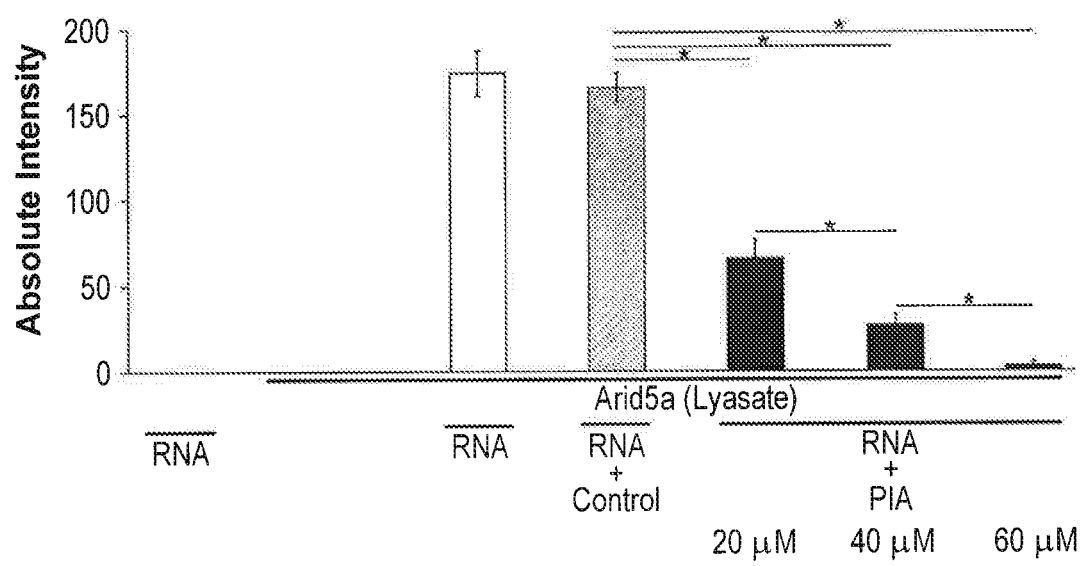
FIG. 1B is a graph showing the absolute intensities of Arid5a protein bands detected in the OX40 ADE-like SL-derived eluates in the presence of PIA.

As shown in FIG. 1A, the PIA inhibited RNA-binding activity of Arid5a to the ADE-like SL in the 3'UTR of OX40 mRNA, in a concentration-dependent manner. FIG. 1B shows that PIA exerts significant reduction in absolute intensities of Arid5a protein bands detected in the OX40 ADE-like SL-derived eluates.

Example 4

STAT3 SL (RNA)-Protein (Arid5a)-Binding Assay

The 3'-biotinylated RNA of STAT3 SL (5'-UGCAGUGGCUUGUGUUCUGGCCACUGCA-3') (SEQ ID NO: 7) was conjugated to streptavidin beads. The biotinylated RNA-streptavidin conjugate was mixed with lysates of HEKT293 cells transfected with pcDNA3.1 expressing Flag-Arid5a (WT) in the absence or presence of scramble peptide (Control: SEQ ID NO: 8) or PIA (SEQ ID NO: 2) (20, 40 and 60 μM), washed, and eluted for detection by immunoblot. Anti-Flag monoclonal antibodies were used to detect Flag-Arid5a in the eluates.

Figure 2A:
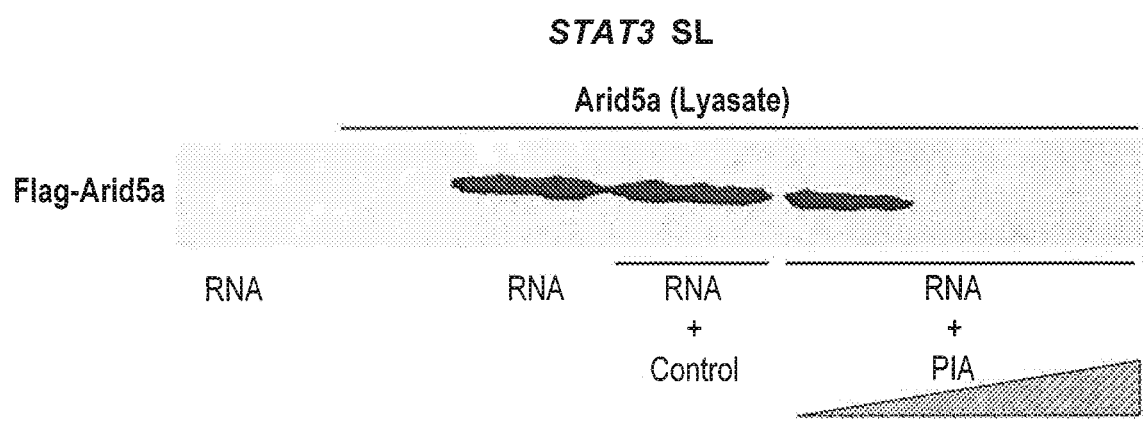
FIG. 2A is an immunoblot image showing the inhibitory effects of PIA on Arid5a (Flag-Arid5a) binding to the SL in STAT3 3'UTR in the presence of PIA.
Figure 2B:
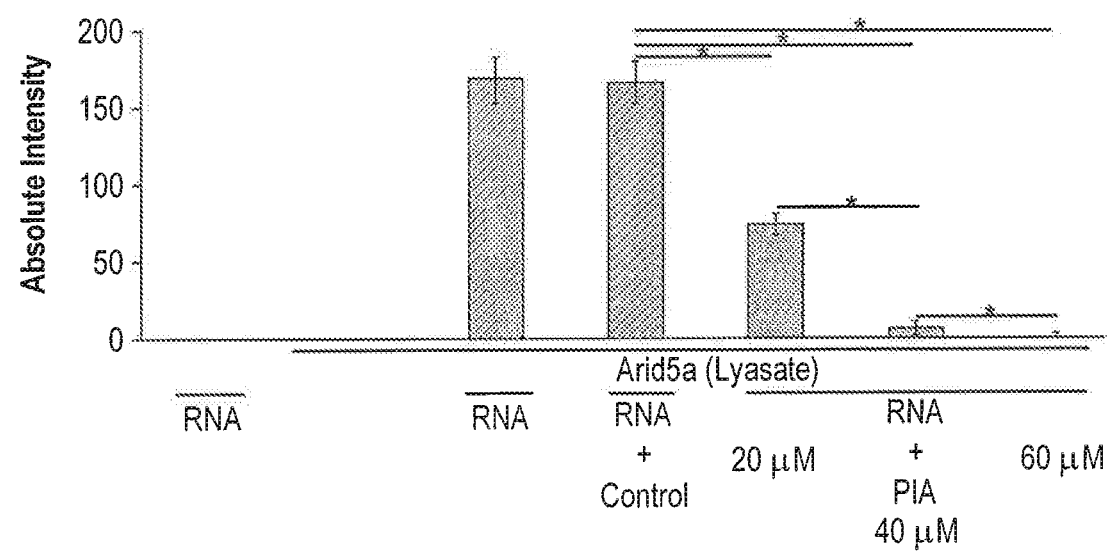
FIG. 2B shows the absolute intensities of Arid5a protein bands detected in the STAT3 SL-derived eluates in the presence of PIA.

FIG. 2A shows that PIA inhibited RNA-binding activity of Arid5a to the identified SL in the 3'UTR of STAT3 mRNA, in a concentration-dependent manner. FIG. 2B shows that PIA exerts significant reduction in absolute intensities of Arid5a protein bands detected in the STAT3 SL-derived eluates.

Example 5

OX40 ADE-Like SL (RNA)-Protein (Mutant Arid5a)-Binding Assay

The 3'-biotinylated RNA of OX40 ADE-like SL (5'-UCCACACCGUUCUAGGUGCUGG-3') (SEQ ID NO: 6) was conjugated to streptavidin beads. The biotinylated RNA-streptavidin conjugate was mixed with lysates of HEKT293 cells transfected with pcDNA 3.1 expressing Flag-Arid5a (WT or mutant) in the presence of scramble peptide (Control; SEQ ID NO: 8) or PIA_(SEQ ID NO: 2) (60 μM), washed, and eluted for detection by immunoblotting. Anti-Flag monoclonal antibodies were used to detect WT and mutant Flag-Arid5a in the eluates. Substitution mutations were introduced to the WT Arid5a at the residues 56-58, 133-134 and 137.

Figure 3A:
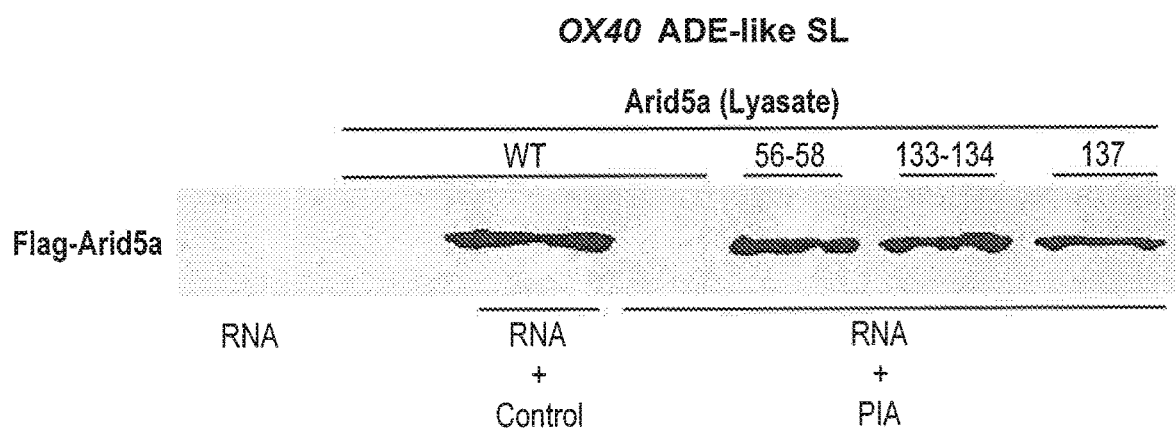
FIG. 3A is an immunoblot image showing the deteriorating effects of mutations in Pocket X on PIA-mediated inhibition of Arid5a (Flag-Arid5a) binding to OX40 ADE-like SL.
Figure 3B:
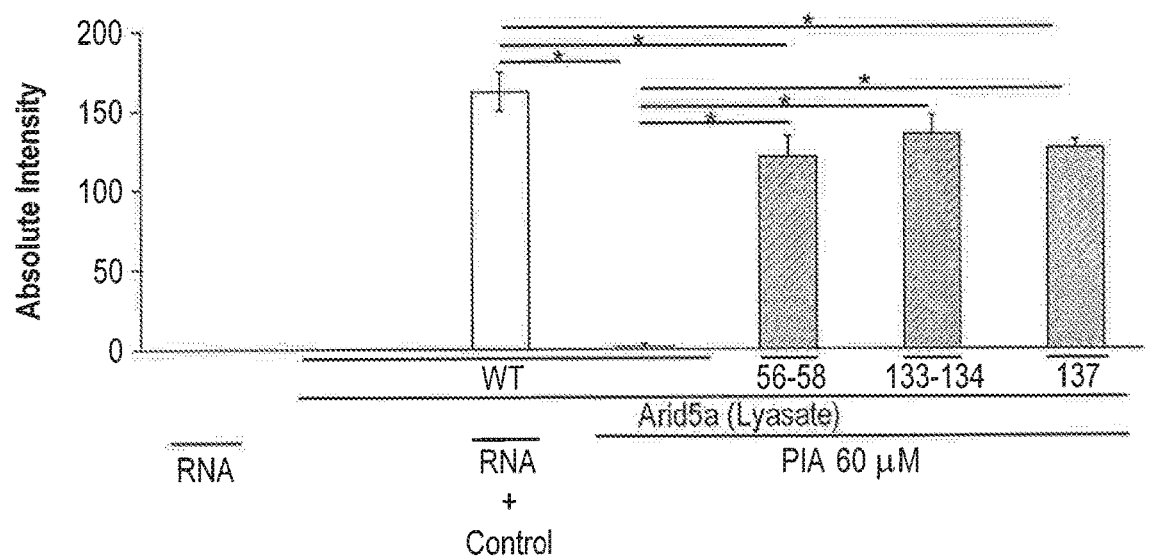
FIG. 3B is a graph showing the absolute intensities of Arid5a (WT and mutant) protein bands detected in the OX40 ADE-like SL-derived eluates in the presence of PIA.

FIG. 3A shows that substitution mutations in the Pocket X residues 56-58, 133-134 and 137 in Pocket X of Arid5a abolished the inhibitory effects of PIA (SEQ ID NO: 2) on the RNA-binding activity of Arid5a to the OX40 ADE-like SL. FIG. 3B shows the absolute intensities of Arid5a protein bands detected in the OX40 ADE-like SL-derived eluates were significantly higher with mutant Arid5a compared with the WT counterpart in the presence of PIA.

Example 6

STAT3 SL (RNA)-Protein (Mutant Arid5a)-Binding Assay

The 3'-biotinylated RNA of STAT3 SL (5'-UGCAGUGGCUUGUGUUCUGGCCACUGCA-3') (SEQ ID NO: 7) was conjugated to streptavidin beads. The biotinylated RNA-streptavidin conjugate was mixed with lysates of HEKT293 cells transfected with pcDNA 3.1 expressing Flag-Arid5a (WT or mutant) in the presence of scramble peptide (Control; SEQ ID NO: 8) or PIA (SEQ ID NO: 2) (60 μM), washed, and eluted for detection by immunoblot. Anti-Flag monoclonal antibodies were used to detect WT and mutant Flag-Arid5a in the eluates. Substitution mutations were introduced to the WT Arid5a at 56-58, 133-134 and 137.

Figure 4A:
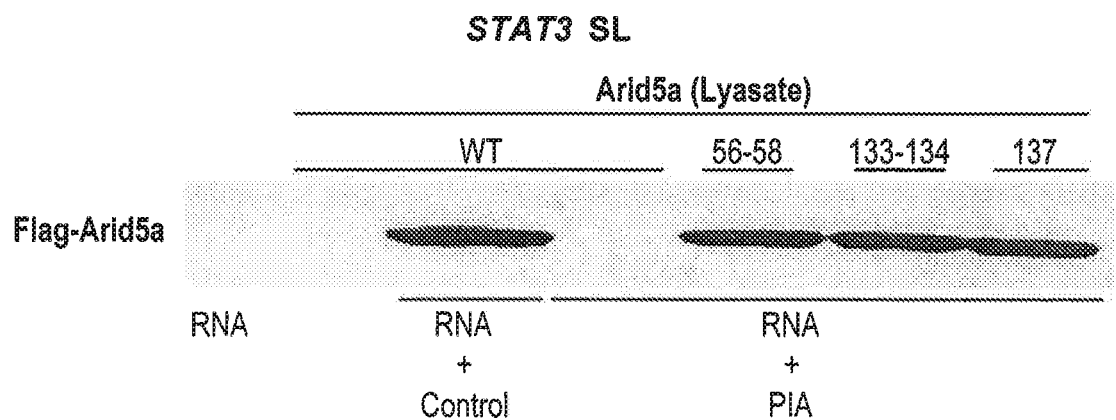
FIG. 4A is an immunoblot image showing the deteriorating effects of mutations in Pocket X on PIA-mediated inhibition of Arid5a (Flag-Arid5a) binding to STAT3 SL.
Figure 4B:
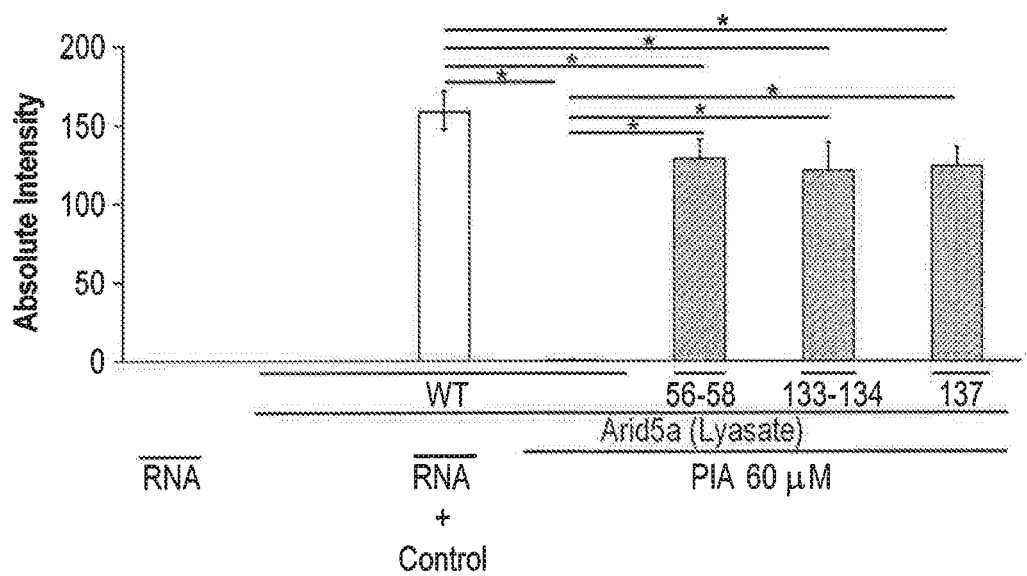
FIG. 4B shows absolute intensities of Arid5a (WT and mutant) protein immunoblot bands detected in the STAT3 SL-derived eluates.

FIG. 4A shows that substitution mutations in the Pocket X residues 56-58, 133-134 and 137 abolished the inhibitory effects of PIA on the RNA-binding activity of Arid5a to the STAT3 SL. FIG. 4B shows the absolute intensities of Arid5a protein bands detected in the STAT3 SL-derived eluate were significantly higher with mutant Arid5a compared with the WT counterpart in the presence of PIA.

Example 7

Evidence on Anti-Inflammatory Effects of PIA

Arid5a plays an important role in the production of IL-17, a cytokine that plays pivotal roles in chronic inflammation and autoimmune diseases such as MS and rheumatoid arthritis, and cancer. Therefore, the effects of PIA (SEQ ID NO: 2) on IL-17 production by naïve $CD4^+$ cells cultured under Th17-polarizing conditions were examined. The $CD4^+CD62L^+$ T cells were cultured in the presence of anti-CD3/CD28 dynabeads, IL-6, TGF-β1, anti-IFN-γ and anti-IL-4.

Figure 5:
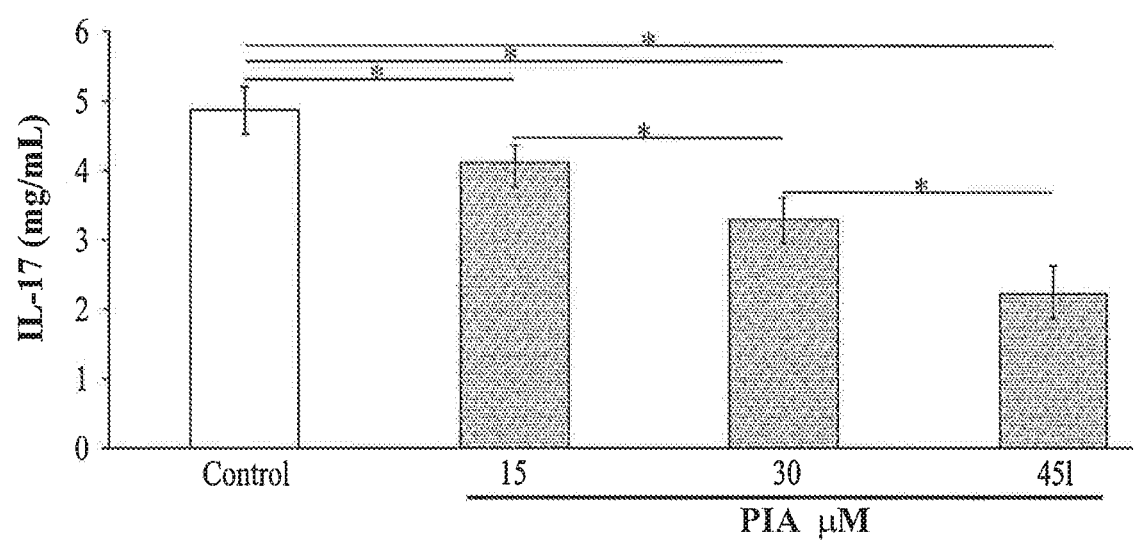
FIG. 5 is a graph showing the suppressive effects of PTA on IL-17 production by naïve CD4$^+$ T cells cultured under Th17-polarizing conditions.

FIG. 5 shows that PIA at 15, 30 and 45 μM reduced IL-17 production by polarized Th17 cells in a concentration-dependent manner. Notably, no significant effects on cell viability were reported.

It is to be understood that the Arid5a peptide inhibitors are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A peptide, consisting of the amino acid sequence of SEQ ID NO: 1.

2. A pharmaceutical composition, comprising: the peptide of claim 1 and a pharmaceutically acceptable carrier.

3. A peptide, comprising at least one sequence selected from the group consisting of SEQ ID NO: 2 and SEQ ID NO: 4.

4. A pharmaceutical composition, comprising: the peptide of claim 3 and a pharmaceutically acceptable carrier.

* * * * *